US006538112B2

(12) United States Patent
Bednar et al.

(10) Patent No.: US 6,538,112 B2
(45) Date of Patent: Mar. 25, 2003

(54) HYBRIDOMAS AND MONOCLONAL ANTIBODIES FOR AN ANTICOAGULANT TEST

(75) Inventors: Bohumil Bednar, North Wales, PA (US); Daniel M. Bollag, Wyncote, PA (US); Robert J. Gould, Green Lane, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/823,444

(22) Filed: Mar. 30, 2001

(65) Prior Publication Data

US 2002/0009753 A1 Jan. 24, 2002

Related U.S. Application Data

(62) Division of application No. 09/170,858, filed on Oct. 13, 1998, now Pat. No. 6,210,904.
(60) Provisional application No. 60/061,839, filed on Oct. 14, 1997.

(51) Int. Cl.$^7$ .......................... C07K 16/00; C12P 21/08
(52) U.S. Cl. ........................... 530/388.22; 530/388.25; 530/388.7; 530/387.1; 435/7.1
(58) Field of Search ................ 530/388.22, 388.25, 530/388.7, 387.1; 435/7.1

(56) References Cited

U.S. PATENT DOCUMENTS

| | | | |
|---|---|---|---|
| 4,717,654 A | | 1/1988 | Savoca et al. |
| 4,798,807 A | * | 1/1989 | Vanderlaan et al. ........ 436/548 |
| 4,810,632 A | | 3/1989 | McMillan |
| 4,943,562 A | * | 7/1990 | Jolles et al. .................. 514/18 |
| 5,114,842 A | | 5/1992 | Plow et al. |
| 5,177,188 A | | 1/1993 | Ginsberg et al. |
| 5,196,308 A | | 3/1993 | Ginsberg |
| 5,225,181 A | | 7/1993 | Srivastava et al. |
| 5,256,538 A | | 10/1993 | Aiken et al. |
| 5,284,751 A | | 2/1994 | Frelinger, III et al. |
| 5,306,620 A | | 4/1994 | Ginsberg |
| 5,318,899 A | | 6/1994 | Scarborough et al. |
| 5,391,704 A | | 2/1995 | McMillan et al. |
| 5,429,925 A | * | 7/1995 | Vanderlaan et al. ......... 435/7.1 |
| 5,470,738 A | | 11/1995 | Frelinger, III et al. |
| 5,578,704 A | * | 11/1996 | Kim et al. ............. 530/388.22 |
| 5,585,243 A | | 12/1996 | Aster et al. |
| 5,656,442 A | | 8/1997 | Ginsberg |
| 5,716,951 A | | 2/1998 | Blackburn et al. |
| 5,736,339 A | | 4/1998 | Scarborough et al. |
| 5,763,201 A | | 6/1998 | Tomer |
| 5,777,085 A | | 7/1998 | Co et al. |
| 5,877,006 A | * | 3/1999 | Coller et al. ............. 435/252.3 |
| 5,877,295 A | * | 3/1999 | Diamond et al. ...... 530/387.73 |
| 5,939,276 A | | 8/1999 | Tomer |
| 5,972,718 A | | 10/1999 | Moghaddam et al. |
| 5,976,532 A | | 11/1999 | Coller et al. |
| 6,210,904 B1 | * | 4/2001 | Bednar ...................... 435/7.1 |

FOREIGN PATENT DOCUMENTS

| | | |
|---|---|---|
| WO | WO 94/11740 | 5/1994 |
| WO | WO 95/08116 | 3/1995 |

OTHER PUBLICATIONS

Curtis et al., Blood, "Antibodies in Sulfonamide–Induced Immune Thrombocytopenia Recognize . . . ", vol. 84(1), pp. 176–183 (1994).
Visentin et al., Transfusion, "Detection of drug–dependent, platelet–reactive antibodies by antigen–capture Elisa and flow cytometry", vol. 30(8), pp. 694–700 (1900).
Newman, Peter J. and Nathalie Valentin, Thrombosis and Haemostatis, " Human Platelet Alloantigens: Recent Findings, New Perspectives", vol. 74(1), pp. 234–239 (1995).
Varon, D. et al., Proc. Natl. Acad. Sci., USA, vol. 80, pp. 6992–6995, Nov. 1983.
Visentin, GP et al., Blood, vol. 77, pp. 2668–2676, No. 12, 1991.
Yano, S. et al., Eur. J. Immunol., vol. 25, pp. 3128–3133, 1995.
International Journal of Clinical Pharmacology, Therapy and Toxicology, "Standardization of definitions and criteria of casualty assessment of adverse drug reactions", vol. 29(2), pp. 75–81, 1991.
Bednar, B. et al., Circulation, vol. 94, (8 suppl.), p. 199, (abstract), 1996.
Curtis. B. R. et al., Transfusion, vol. 33, No. 9, pp. PS 77 (abstract), 1992.
Mousa et al., Drugs of the Future, "Platelets in health and disease: platelet GPIIb–IIIa structure and function: recent advances in antiplatelet therapy", vol. 21 (11), pp. 1141–1154, 1996.
Shiba, E. et al., Am. J. Physiol., vol. 260 (5 part 1), pp. C965–C974, 1991.
Connelian, J. M. et al., Thrombosis Research, vol. 61, pp. 501–514, 1991.
Bednar, R. A. et al., Circulation, vol. 94(8), supplement 1, p. 1–98, abstract 0568, Oct. 15, 1994.
Frelinger, A. et al., J. Biol. Chem., vol. 265(11), pp. 6346–6352 (abstract), Apr. 15, 1990.

(List continued on next page.)

*Primary Examiner*—Lynette R. F. Smith
*Assistant Examiner*—Ginny Allen Portner
(74) *Attorney, Agent, or Firm*—Richard S. Parr; Melvin Winokur; Valerie J. Camara

(57) ABSTRACT

The present invention is a method for diagnosing a patient at risk to thrombocytopenia induced by administration of a GP IIb/IIIa receptor antagonist, which comprises combining
  i) a plasma sample of the patient;
  ii) detectable monoclonal antibody which recognizes induced binding sites formed on the GP IIb/IIIa receptor following association of a fibrinogen receptor antagonist with the GP IIb/IIIa receptor; and
  iii) GP IIb/IIIa receptor:GP IIb/III receptor antagonist complex,
and determining association of the detectable monoclonal antibody with the complex in the presence of the plasma.

6 Claims, No Drawings

OTHER PUBLICATIONS

Tcheng, J. E., American Journal of Cardiology, vol. 78 (3a), pp. 35–40, Aug. 16, 1996.

Askew, B. C. et al., Book of Abstract, 214th ACS National Meeting, section MEDI, abstract 117, Sep. 7–11, 1997.

Skogen et al., Transfusion, "Rapid determination of platelet alloantigen genotypes by polymerase chain reaction using allele–specific primers", vol. 34(11), pp. 955–960 (1994).

McFarland et al., Blood, "Neonatal Alloimmune Thrombocytopenia Due to a New Platelet–Specific Alloantibody", vol. 81(12), pp. 3381–3323 (1993).

Kunicki, Thomas J. and Newman, Peter J., Blood, "The Molecular immunology of Human Platelet Proteins", vol. 80(6), pp. 1386–1404 (1992).

Khaspekova, SG. et al., Biokhimiia, vol. 61(3), pp. 412–428, (abstract), Mar. 1996.

Mazurov, AV. et al., Febs Letters, vol. 391 (1–2), pp. 84–88, (abstract), Aug. 5, 1996.

Honda, Sehal, J. Biol. Chem, vol. 270(20) pp. 11947–11954, (abstract), May 19, 1995.

Tsubakio et al., British J. Haematol, vol. 67, pp. 345–348, (1987).

Kovasovics TJ et al., J. Biol. Chem., vol. 270(19) pp. 11358–11366, (abstract), May 12, 1995.

* cited by examiner

```
                          SEQUENCE LISTING

<160> NUMBER OF SEQ ID NOS: 6

<210> SEQ ID NO 1
<211> LENGTH: 6
<212> TYPE: PRT
<213> ORGANISM: Unknown
<220> FEATURE:
<221> NAME/KEY: UNSURE
<222> LOCATION: 1
<223> OTHER INFORMATION: Xaa=acetimidyl-lysine
<223> OTHER INFORMATION: Xaa=acetimidyl-lysine.   This sequence is
      synthetically prepared.

<400> SEQUENCE: 1

Xaa Gly Asp Trp Phe Cys
 1               5

<210> SEQ ID NO 2
<211> LENGTH: 6
<212> TYPE: PRT
<213> ORGANISM: Unknown
<220> FEATURE:
<221> NAME/KEY: UNSURE
<222> LOCATION: 1
<223> OTHER INFORMATION: Xaa = acetylimidyl-lysine
<221> NAME/KEY: UNSURE
<222> LOCATION: 6
<223> OTHER INFORMATION: Xaa = penicillamine
<223> OTHER INFORMATION: Xaa=acetimidyl-lysine.   This sequence is
      synthetically prepared.
      Xaa = penicillamine.  This sequence is
      synthetically prepared.

<400> SEQUENCE: 2

Xaa Gly Asp Trp Phe Xaa
 1               5

<210> SEQ ID NO 3
<211> LENGTH: 6
<212> TYPE: PRT
<213> ORGANISM: Unknown
<220> FEATURE:
<221> NAME/KEY: UNSURE
<222> LOCATION: 1
<223> OTHER INFORMATION: Xaa = phenylimidyllysine
<221> NAME/KEY: UNSURE
<222> LOCATION: 6
<223> OTHER INFORMATION: Xaa = penicillamine
<223> OTHER INFORMATION: Xaa = phenylimidyllysine.  This sequence is
      synthetically prepared.
      Xaa = penicillamine.  This sequence is
      synthetically prepared.

<400> SEQUENCE: 3

Xaa Gly Asp Trp Phe Xaa
 1               5

<210> SEQ ID NO 4
<211> LENGTH: 6
<212> TYPE: PRT
<213> ORGANISM: Unknown
<220> FEATURE:
<221> NAME/KEY: UNSURE
```

```
<222> LOCATION: 1
<223> OTHER INFORMATION: Xaa = phenylimidyllysine
<223> OTHER INFORMATION: Xaa = phenylimidyllysine.  This sequence is
      synthetically prepared.

<400> SEQUENCE: 4

Xaa Gly Asp Trp Phe Cys
 1               5

<210> SEQ ID NO 5
<211> LENGTH: 7
<212> TYPE: PRT
<213> ORGANISM: Artificial Sequence
<220> FEATURE:
<223> OTHER INFORMATION: This sequence is a synthetically prepared
      peptide.

<400> SEQUENCE: 5

Cys Asn Pro Arg Gly Asp Cys
 1               5

<210> SEQ ID NO 6
<211> LENGTH: 4
<212> TYPE: PRT
<213> ORGANISM: Artificial Sequence
<220> FEATURE:
<223> OTHER INFORMATION: This sequence is a synthetically prepared
      peptide.

<400> SEQUENCE: 6

Arg Gly Asp Ser
 1
```

HYBRIDOMAS AND MONOCLONAL ANTIBODIES FOR AN ANTICOAGULANT TEST

This is a division of application Ser. No. 09/170,858, filed Oct. 13, 1998 now U.S. Pat. No. 6,210,904 claims the benefit under Title 35 United States Code 119(e) of U.S. provisional application No. 60/061,839, filed Oct. 14, 1997.

BACKGROUND OF THE INVENTION

Drug-induced thrombocytopenia contributes to morbidity and, occasionally, mortality in patients treated with a wide range of medications (Karpatkin, (1971) *Am. J. Med. Sci.* 262, p. 68). More than 100 different medications have been implicated in drug-induced thrombocytopenia, including heparin, quinine, quinidine and sulfonamide antibiotics (Shulman et al. "Hemostasis and Thrombosis" (ed 2) Philadelphia, Pa., Lippincott (1987) p.452, and Kracke et al. (1943) *JAMA* 122, p. 168.

Drug-dependent antibodies reactive with platelets have been identified in only a few instances. Curtis et al., (1984) *Blood* v. 84, n.1, 176–183, applied flow cytometry to the detection of such antibodies induced by sulfonamide antibiotics. Visentin et al. (1990) *Transfusion* Oct. v. 30 n. 8, 694–700 describes detection of drug-dependent, platelet-reactive antibodies by antigen-capture ELISA and flow cytometry.

The occurrence of fibrinogen receptor antagonist induced-thrombocytopenia has prompted a search for monoclonal antibodies (mAbs) specific for GP IIb/IIIa receptor:receptor antagonist complexes. Monoclonal antibodies capable of detecting alterations in glycoprotein IIb/IIIa upon binding of fibrinogen receptor antagonists to glycoprotein IIb/IIIa are useful in diagnosing patients at risk to developing fibrinogen receptor antagonist-induced thrombocytopenia. The monoclonals can be tagged with fluorescent or radioactive tracers for ease in diagnosis.

The present invention includes monoclonal antibodies which recognize induced binding sites formed on GPIIb/IIIa receptor following association of a fibrinogen receptor antagonist with the GPIIb/IIIa receptor, and a means for identifying, in a patient, the presence of one or more antibodies in GP IIb/IIIa receptor (fibrinogen receptor) antagonist-induced thrombocytopenia which recognize GPIIb/IIIa receptor:GPIIb/IIIa receptor antagonist complexes formed with purified platelets or purified GPIIb/IIIa receptor and a selected GPIIb/IIIa receptor antagonist. Identification of such antibodies identifies the patient as being at risk to development of thrombocytopenia resulting from administration to the patient of the selected GP IIb/IIIa receptor antagonist.

Diagnosis of patients at risk to developing fibrinogen receptor antagonist induced-thrombocytopenia can be implemented using monoclonal antibodies, having fluorescent, nuclear magnetic or radioactive tags, which are specific for GP IIb/IIIa receptor:receptor antagonist complexes. These monoclonal antibodies will associate with the complex unless a patient's plasma sample, when mixed with the complex and the monoclonal antibody, prevents association of the complex with the monoclonal antibody.

SUMMARY OF THE INVENTION

The invention includes isolated monoclonal antibodies or detectable monoclonal antibodies which recognize induced binding sites formed on the GP IIb/IIIa receptor following association of a fibrinogen receptor antagonist with the GP IIb/IIIa receptor. Exemplary monoclonal antibodies of the invention include mAb10-758 and mAb15-758. The invention also includes humanized forms of the monoclonal antibodies.

The invention is also a hybridoma cell line selected from the group consisting of DD6 and FB3, which cell lines produce monoclonal antibodies of the invention, e.g. mAb10-758, and mAb15-758.

The invention is also a method for diagnosing a patient at risk to thrombocytopenia induced by administration of a GP IIb/IIIa receptor antagonist, which comprises combining i) a plasma sample of the patient;

ii) detectable monoclonal antibody which recognizes induced binding sites formed on the GP IIb/IIIa receptor following association of a fibrinogen receptor antagonist with the GP IIb/IIIa receptor; and iii) GP IIb/IIIa receptor:GP IIb/III receptor antagonist complex, and determining association of the detectable monoclonal antibody with the complex in the presence of the plasma. The monoclonal antibodies, e.g. detectable mAb10-758 and detectable mAb15-758, are made detectable by labeling, e.g., with a fluorescence label.

In one class of the method for diagnosing a patient at risk to thrombocytopenia induced by administration of a GP IIb/IIIa receptor antagonist, the fibrinogen receptor antagonist is selected from the group consisting of Mpr-(Acetimidyl-Lys)-Gly-Asp-Trp-Phe-Cys-NH$_2$, Mpr-(Acetimidyl-Lys)-Gly-Asp-Trp-Phe-Pen-NH$_2$, Mpr-(Phenylimidyl-Lys)-Gly-Asp-Trp-Phe-Pen-NH$_2$, Mpr-(Phenylimidyl-Lys)-Gly-Asp-Trp-Phe-Cys-NH$_2$, N-Methyl-D-phenylalanyl-N-[(1S)-1-formyl-4-guanidinobutyl]-L-prolinamide, ((1-(2-((4-(aminoiminomethyl)benzoyl)amino)-3-(4-hydroxyphenyl)-1-oxopropyl)-4-piperidinyl)oxy)-(S)-acetic acid, Ethyl 3-[[4-[[4-(aminoiminomethyl)phenyl]amino]-1,4-dioxobutyl]amino]-4-pentynoate, N-(2-(2-(((3-((aminoiminomethyl)amino)propyl)amino)carbonyl)-1-piperidnyl)-1-(cyclohexylmethyl)-2-oxoethyl)-(R,S)-glycine, (2-S-(n-Butylsulfonylamino)-3[4-(piperidin-4-yl)butyloxyphenyl]propionic acid hydrochloride, Ethyl 3-[[4-[[4-(aminoiminomethyl)phenyl]amino]-1,4-dioxobutyl]amino]-4-pentynoate, 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid, (R)-methyl-3-[[[3-[4-(aminoiminomethyl)phenyl]-4,5-dihydro-5-isoxazolyl]acetyl]amino]-N-(butoxycarbonyl)-L-alanine monoacetate, and

[3(R)-[2-Piperidin-4-yl)ethyl]-2-piperidone-1]acetyl-3(R)-methyl-β-alanine, and pharmaceutically acceptable salts thereof.

The invention is also a test kit for diagnosing a patient at risk to thrombocytopenia induced by administration of a GP IIb/IIIa receptor antagonist, which comprises a GP IIb/IIIa receptor:GP IIb/III receptor antagonist complex, and a detectable monoclonal antibody which recognizes induced binding sites formed on the GP IIb/IIIa receptor following association of a fibrinogen receptor antagonist with the GP IIb/IIIa receptor.

The invention is also a method for identifying a patient not at risk to developing fibrinogen receptor antagonist-induced thrombocytopenia which comprises combining i) patient plasma;

ii) a detectable monoclonal antibody which recognizes induced binding sites formed on the GP IIb/IIIa receptor following association of a fibrinogen receptor antagonist with the GP IIb/IIIa receptor; and iii) a GPIIb/IIIa receptor:GPIIb/IIIa receptor antagonist complex, to form a GPIIb/IIIa receptor:GPIIb/IIIa receptor antagonist:detectable monoclonal antibody complex, and detecting the presence of the detectable monoclonal antibody in the GPIIb/IIIa receptor:GPIIb/IIIa receptor antagonist:detectable monoclonal antibody complex.

The invention is also a method for identifying a patient at risk to developing fibrinogen receptor antagonist-induced thrombocytopenia which comprises combining i) patient plasma;

ii) a detectable monoclonal antibody which recognizes induced binding sites formed on the GP IIb/IIIa receptor following association of a fibrinogen receptor antagonist with the GP IIb/IIIa receptor; and iii) a GPIIb/IIIa receptor:GPIIb/IIIa receptor antagonist complex, to form a reaction product, and detecting the absence of the detectable monoclonal antibody in the reaction product.

DETAILED DESCRIPTION OF THE INVENTION

The anti-GPIIb/IIIa antibodies against purified GPIIb/IIIa associated with a potent fibrinogen receptor antagonist are specific to the $\beta_3$ subunit and are able to recognize this subunit on endogenous $\alpha_{IIb}\beta_3$ and $\alpha_v\beta_3$ integrins as shown by immunoprecipitation.

These antibodies recognize ligand-induced binding sites formed on the receptor following association of a fibrinogen receptor antagonist with the GP IIb/IIIa receptor. Specific examples of such monoclonal antibodies include mAb10-758 and mAb15-758.

mAb10-758 binding affinity to resting platelets is increased in the presence of ligand and its binding induces platelet aggregation and PAC-1 (Platelet Activation Complex-1) binding to resting platelets in the absence of platelet activation. Therefore, mAb10-758 is an anti-LIBS antibody. The term "LIBS" means "ligand induced binding sites."

mAb15-758 represents a potent anti-LIBS antibody. The binding affinity of this antibody to GPIIb/IIIa is very weak on resting and ADP activated platelets. mAb15-758 binding can be increased by the disassociation of the GPIIb/IIIa complex or by occupying the receptor with RGDS containing ligands. Like mAb10-758, mnAb15-758 is able to activate the GPIIb/IIIa complex in the absence of platelet activation.

Our results demonstrate that potent fibrinogen receptor antagonists tested, including RO-44-9883 ({1-[2-(4-carbamimidoyl-benzylamino)-3-(4-hydroxyphenyl)-propionyl]-piperidin-4-yloxy}-acetic acid), induce the neo-epitope which is recognized by mAb15-758.

The selected GP IIb/IIIa receptor antagonist suitable for the methods of the invention is any antagonist which is useful for inhibiting fibrinogen binding to the GP IIb/IIIa platelet receptor. Such antagonists are well known in the art.

The following abbreviations are used in the description: LIBS (ligand induced binding sites); RO-44-9883 ({1-[2-(4-carbamimidoyl-benzoylamino)3-(4-hydroxy-phenyl)propionyl]-piperidin-4-yloxy}-acetic acid); PAC-1 (Platelet Activation Complex-1); and GFP (gel filtered platelets).

Antagonists for the GP IIb/IIIa receptor have been described in, for example, U.S. Pat. Nos. 5,470,849, 5,463,011, 5,455,243, 5,451,578, 5,446,056, 5,441,952, 5,422,249, 5,416,099, 5,405,854, 5,397,791, 5,393,760, 5,389,631, 5,380,713, 5,374,622, 5,358,956, 5,344,783, 5,340,798, 5,338,7235,334,596, 5,321,034, 5,318,899 (e.g. cyclic heptapeptides Mpr-(Acetimidyl-Lys)-Gly-Asp-Trp-Phe-Cys-NH$_2$, Mpr-(Acetimidyl-Lys)-Gly-Asp-Trp-Phe-Pen-NH$_2$, Mpr-(Phenylimidyl-Lys)-Gly-Asp-Trp-Phe-Pen-NH$_2$, and Mpr-(Phenylimidyl-Lys)-Gly-Asp-Trp-Phe-Cys-NH$_2$, wherein Mpr is mercapto propionyl), U.S. Pat. Nos. 5,312,923, 5,294,616, 5,292,756 (e.g. 2-S-(n-Butylsulfonylamino)-3[4-piperidin-4-yl)butyloxyphenyl] propionic acid hydrochloride), U.S. Pat. No. 5,281,585 (e.g. [3(R)-[2-Piperidin-4-yl)ethyl]-2-piperidone-1]acetyl-3(R)-methyl-$\beta$-alanine), U.S. Pat. Nos. 5,272,158, 5,264,420, 5,260,307, 5,239,113 (e.g. Ethyl 3-[[4-[[4-(aminoiminomethyl)-phenyl]amino]-1,4-dioxobutyl] amino]-4-pentynoate), U.S. Pat. Nos. 5,227,490, 5,206,373, 4,703,036 (e.g. N-Methyl-D-phenylalanyl-N-[(1S)-1-formyl-4-guanidinobutyl]-L-prolinamide), EP 505 868 (e.g. ((1-(2-((4(aminoiminomethyl)benzoyl)amino)-3-(4-hydroxyphenyl)-1-oxopropyl)-4-piperidinyl)oxy)-(S)-acetic acid), WO 9311152 (e.g. N-(2-(2-(((3-((aminoiminomethyl) amino)propyl)amino)-carbonyl)-1-piperidnyl)-1-(cyclohexylmethyl)-2-oxoethyl)-(R,S)-glycine), WO 9418981 (e.g. 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino] propionic acid), WO 9514683 (e.g. methyl-N$^3$-[2-{3-(4-formamidinophenyl)-isoxazolin-5(R)-yl}-acetyl]-N$^2$-(n-butyloxycarbonyl)-2,3-(S)-diaminopropionate acetate salt), EP 333 356 and WO 9422820. They are described as useful for inhibiting fibrinogen binding and inhibiting clot formation.

GP IIb/IIIa ($\alpha_{IIb}\beta_3$) is a member of the integrin family of adhesive receptors and plays a vital role in thrombosis and hemostatis by serving as the receptor for the adhesive proteins fibrinogen, vitronectin, Von Willebrand factor, and fibronectin on platelets (Haverstick et al. (1995) Blood 66, 946–952; Savage et al. (1991) J. Biol. Chem. 266, 11227–11233; Phillips et al. (1991) Cell 65, 359–362). During the processes of cell attachment, spreading and platelet aggregation $\alpha_{IIb}\beta_3$ progresses through several functional states which reflect conformational changes in the receptor (Plow et al. (1991) Prog. Hemastasis Thrombosis 9, 117–156). On unactivated platelets, $\alpha_{IIb}\beta_3$ cannot bind soluble fibrinogen (Peerschke (1985) Seminars Heamatol 22, 241–259). However, upon platelet activation, $\alpha_{IIb}\beta_3$ undergoes a conformational change exposing a common ligand binding site for fibrinogen, fibronectin and Von Willebrand factor (Lam et al. (1987) J. Biol. Chem. 262, 947–950) that recognizes a small peptide sequence on the peptide (Loftus et al. (1990) Science 249, 915–918).

The binding of ligands to GP IIb/IIIa induces additional conformational changes of the extracellular domains of the receptor (Parise et al. (1987) J. Biol. Chem. 262, 12597–12602) leading to post receptor occupancy events and the exposure of neo-epitopes (LIBS) (Frelinger et al. (1988) J. Biol. Chem. 263, 12397–12402). Anti-LIBS antibodies have been generated against LIBS sites on both the $\alpha_{IIb}$ and $\beta_3$ subunits (Frelinger et al. (1988) J. Biol. Chem., 263, 12397–12402; Frelinger et al. (1990) J. Biol. Chem., 265, 6346–6352; Kouns et al. (1990) J. Biol. Chem. 265, 20594–20604; Honda et al. (1995) J. Biol. Chem. 270, 11947–11954; Satoh et al. (1991) Biochem. J. 301, 785–791; Frelinger et al. (1991) J. Biol. Chem. 266, 17106–17111).

The epitopes exposed by ligand binding have functional importance in ligand affinity (Frelinger et al. (1990) *J. Biol. Chem.* 265, 6346–6352; Frelinger et al. (1991) *J. Biol. Chem.* 266, 17106–17111; Moderna et al. (1994) *Clinical Research* 42, 131a); platelet aggregation (Kouns et al. (1990) *J. Biol. Chem.* 265, 20594–20604; Frelinger et al. (1991) *J. Biol. Chem.* 266, 17106–17111); clot retraction (Frelinger et al. (1990) *J. Biol. Chem.* 265, 6346–6352), and cellular adhesion (Frelinger et al. (1988) *J. Biol. Chem.* 263, 12397–12402; Frelinger et al. (1990) *J. Biol. Chem.* 265, 6346–6352; Shadle et al. (1984) *J. Cell. Bio.* 99, 2056–2060).

The conformationally restrained LIBS epitope is modulated by ligand binding to $\alpha_{IIb}\beta_3$. Binding of natural ligands (Heath et al. (1994) *Annals of The New York Academy of Sciences* 714, 300–302; Mondoro et al. (1996) *Blood* 88, 3824–3830), non peptide ligands (Satoh et al. (1991) *Biochem J.* 301, 785–791; Kouns et al. (1993) *Thrombosis and Haemostasis* 785), ligand mimetic peptides (Parise et al. (1987) *J. Biol. Chem.* 262, 12597–12602) and antibodies (Tomiyama et al. (1992) *J. Biol. Chem.* 267, 18085–18092) have been shown to induce conformational changes in the extracellular domain of GPIIb/IIIa that are recognized by conformation-dependent anti-LIBS antibodies. Small molecules which inhibit platelet aggregation may be an effective antithrombotic treatment (Gould (1994) "Perspectives in Drug Discovery and Design 1"537–548). Alloantibodies against platelet proteins, including epitopes on GPIIb/IIIa, have been identified in cases of autoimmune thrombocytopenic purpura (Woods et al. (1984) *Blood* 63, 368–375; Bierling et al. (1994) *British Journal of Haematology* 87, 631–633). The conformational changes induced by receptor occupancy of one integrin can influence the function of another distinct integrin within the same cell (Diaz-Gonzalez, et al. (1996) *Molecular Biology of the Cell* 7, 1929–1951). Therefore, it is of interest to examine the capability of various potent peptidometitic inhibitors of platelet aggregation to induce neo-epitopes. Steiner et al. (1993) Thrombosis and Haemostasis, 782, suggests that one such inhibitor, RO 44-9883, does not change the conformation of GPIIb/IIIa upon binding to the receptor. In the present invention, a series of monoclonal antibodies was generated against purified $\alpha_{IIb}\beta_3$ in the presence of a potent RGD-mimetic.

Three antibodies and their binding affinities to GPIIb/IIIa in the presence of various GPIIb/IIIa antagonist were characterized. In contrast to the previous study, we have found that all potent GPIIb/IIIa antagonists induce the neo-epitope which is recognized by anti-LIBS monoclonal antibodies, e.g., mAb10-758 and mAb15-758.

Purification of Proteins

GPIIb/IIIa was purified from outdated human plasma using a slight modification of the procedure described by Kouns et al. (Kouns et al. (1992) *J. Biol. Chem.* 267, 18844–18851). Briefly, detergent solubilized platelet lysates were passed over a Concanavalin A-Sepharose 4B column (Sigma Chemicals, St. Louis, Mo.), followed by elution with methyl-α-D mannopyranozide (Sigma Chemical, St. Louis, Mo.). The eluate from the Concanavalin A column was passed through an RGDS-Sepharose affinity chromatography to purify the active form of the protein. Flow-through from the RGDS column was passed through a Sephacyl S-300 size exclusion column (Sigma Chemical, St. Louis, Mo.) to isolate the inactive form of the protein. All fractions were analyzed for purity by SDS-PAGE electrophoresis.

Antibody Production

The Köhler and Milstein technique introduced in 1975 allows production of unlimited quantities of antibody of precise and reproducible specificity. Conventional polyclonal antisera contain a myriad of different antibodies differing in their specificity and properties, whereas a hybridoma produces a single monoclonal antibody with uniform characteristics. The Köhler-Milstein technique starts with the immunization of an animal with subsequent fusion of spleen cells isolated from the immunized animal with an immortal myeloma cell line. These fused cells (hybridomas) grow in culture, and specific clones can be selected producing the mAb of the desired specificity. Each clone produces one specific monoclonal antibody. These hybridomas can be cultured and/or stored in liquid nitrogen. Thus a constant supply of pure antibody, i.e., monoclonal antibody, is assured.

Antibody proteins recognize specific antigens in an immunological response. Antibody molecules usually recognize a specific region of the antigen known as an epitope or determinant.

Monoclonal antibodies to different cell types have been developed. See for example, Old, Lloyd J. et al. (1981) *Cancer Res.* 41: 361–375, and Eisinger et al. (1982) *Proc. Nat'l. Acad. Sci. USA* 79: 2018.

Gel Filtration of Platelets and Cell Lines:

Gel filtered platelets (GFP) were prepared from blood anticoagulated with 13 mM trisodium citrate. Platelet rich plasma was generated by centrifigation at 180×G for 20 minutes in the presence of 1 $\mu$M PGE$_1$. Platelets were separated from plasma by gel filtration through a Sepharose 2B column (Pharmacia Biotech, Sweden) equilibarated in platelet buffer (NaCl (140 mM), KCL (60 mM), Na$_2$HPO$_4$ (1.9 mM). HEPES (6.7 mM), dextrose (1 mg/ml), and BSA (2%) pH 7.4). The platelets were diluted to 2×10$^8$ cells/mL in platelet buffer before use.

Human erythroleukemia (HEL) cells and Human embryonic kidney (HEK) 293 cells (Abraham et al. (1997) *Molecular Pharmacology* 52, 227–236) were obtained from American Type Collection (ATCC, Rockville, Md.). Human venous endothelial cells (HUVEC) were purchased from Cell Systems (Kirkland, Wash.). Recombinant HEK-$\alpha_{IIb}\beta_3$ cells are described in Abraham et al. (1997) *Molecular Pharmacology* 52, 227–236. Recombinant HEK-$\alpha_v\beta_3$ cells are also described in (Abraham et al. (1997) *Molecular Pharmacology* 52, 227–236).

Synthetic Peptides

Non-potent GPIIb/IIIa ligands 4-(N-piperazine)benzoyl-(N-1,2,3,4-tetrahydroisoquinoline-7-yl)oxy-acetic acid (compound A); and potent fibrinogen receptor antagonists, tirofiban (compound 1–9 in U.S. Pat. No. 5,292,756, the name of which is 2-S-(n-Butylsulfonylamino)-3[4-(piperidin-4-yl)butyloxyphenyl]-propionic acid hydrochloride); cyclo-4-I-benzoyl-(Cys-Asn-Pro-Arg-Gly-Asp-Cys)-OH HOAc salt (compound B), N-[3(R)-[2-(Piperidin-4-yl)ethyl]-2-piperidon-1-yl] acetyl-3(R)-methyl-β-alanine (compound C), and 2-(S)-(3-pyridylsulfonyl)amino-3-N-[5-[2-(4-piperidinyl)ethyl]-thienothiophene-2-carboxamide]propionic acid (compound D) were evaluated for binding affinity. The binding affinities of these compounds to purified human platelet $\alpha_{IIb}\beta_3$ is summarized in Table 1.

TABLE 1

Disassociation constants of GP IIb/IIIa antagonist on purified human $\alpha_{IIb}\beta_3$

| Compound | Activated Form $K_D$-A nM | Unactivated Form $K_D$-B nM |
| --- | --- | --- |
| compound A | >>100,000 | >>100,000 |
| echistatin | 4.6 | 4.9 |
| tirofiban | 2 | 13 |
| compound B | 1.5 | 60 |
| RO-44-9993 | 0.96 | 6.3 |
| compound C | 4.5 | 610 |
| RGDS | 1000 | 1000 |
| compound D | 0.03 | 2.4 |

RO044-9883 ({1-[2-(4-carbamimidoyl-benzoylamino)3-(4-hydroxy-phenyl)propionyl]-piperidin-4-yloxy}-acetic acid) is described in Kouns et al. (1992) J. Bio. Chem. 267, 18844–18851); echistatin is described in Gan et al. (1988) J. Biol. Chem. 263, 19827–19827 and Garsky et al. (1989) Proc. Nat'l. Acad. Sci./USA 86, 4022–4026. RGDS was purchased from Sigma Chemical Company (St. Louis, Mo.).

Production and Purification of Monoclonal Antibodies

Purified human GPIIb/IIIa was purchased from Enzyme Research Laboratories (South Bend, Ind.). Monoclonal antibodies were generated using approximately 1 µM of purified GPIIb/IIIa in the presence of 10 µM of 2-(S)-(3-pyridylsulfonyl)amino-3-N-[5-[2-(4-piperidinyl)ethyl]-thienothiophene-2-carboxamide]propionic acid as the immunogen for BALB/c mice. Sera samples from the mice were screened using ELISA for antibodies against immobilized GPIIb/IIIa. Hybridomas were generated using the mouse with the highest titer. Supernates from the hybridoma fusion were screened for antibodies using ELISA against immobilized GPIIb/IIIa. Hybridoma supernates with the highest titer were further testing for binding to gel filtered platelets using flow cytometry. Briefly, 100 µl of GFP (2×10$^8$ cells/mL) were incubated with flow cytometry buffer (10 mM Hepes, 5 mM KCl, 145 mM NaCl and 1 nM MgCl) or 20 µM 2-(S)-(3-pyridylsulfonyl)amino-3-N-[5-[2-(4-piperidinyl)ethyl]-thienothiophene-2-carboxamide] propionic acid for 15 minutes, followed by the addition of 5 µL of hybridoma supernate. Samples were incubation at room temperature for 1 hour. Bound antibodies were separated from free antibodies by centrifugation in the presence of 100 µM PGE$_1$ (Sigma Chemical, St. Louis, Mo.) followed by resuspension in flow cytometry buffer containing 100 µM FITC conjugated goat anti-mouse IgG (Jackson Immunoresearch Laboratories, West Grove, Pa.). Following incubation for 1 hr at room temperature, the sample was analyzed by flow cytometry using the FACSCaliber system, Becton Dickinson (Franklin Lakes, N.J.). The light scatter and fluorescent intensity of 20000 cells was collected using logarithmic gain.

Several hybridomas which showed an increased fluorescence in the presence of ligand, and one which did not show such increase, were subcloned. The single cell clones were tested using the flow cytometry assay described above. Monoclonal antibodies of interest were purified from ascites fluid by passage through a Protein G-Sepharose column (Pierce, Rockford, Ill.). Purified antibodies were quantitated by amino acid analysis and isotyped using the Isostrips test kit purchased from Boehringer Mannheim Corporation (Indianapolis, Ind.).

Gel Electrophoresis and Western Blotting

Purified GPIIb/IIIa (10 µg) was subject to electrophoresis through an 8% SDS-PAGE (Novex (San Diego, Calif.)) under nonreducing conditions. The proteins were transferred to nitrocellulose membranes and reacted with purified antibody. Bound antibody was detected by sheep anti-mouse, Ig horse radish peroxidase conjugate (Amersham (Arlington Heights, Ill.)). Proteins were visualized using the Renaissance chemiluminescence system (Dupont-NEN (Boston, Mass.)).

Surface Labeling and Immunoprecipitation

2×10$^6$ cells or 2×10$^7$ platelets were surfaced labeled with 5 mM Immunopure-Sulfo-NHS-LC-Biotin (Pierce, Rockford, Ill.) and then solubilized in RIPA buffer (50 mM Tris, pH 7.5, 150 mM NaCl, 1 mM CaCl, 1% NP-40, 0.5% Deoxycholate, 0.1% Sodium Dodecyl Sulfate) containing 1 mM phenylmethylsulfonyl fluoride, 10 µg/ml aprotinin, and 100 µg/mL leupeptin. Cell extracts were precleared with Pansorbin (CalBiochem, (La Jolla, Calif.)) and immunoprecipitated overnight with 5 µg of antibody followed by the addition of goat anti-mouse IgG-sepharose-4B beads (Organon Teknika Corporation (Durham, N.C.)). The anti mouse-sepharose beads were pelleted and washed in RIPA buffer, resuspended in reducing sample buffer containing 6 mM 2-mercaptoethanol and boiled for 5 minutes. The proteins were resolved on an 8% SDS-PAGE and transferred to nitrocellulose. Following transfer the proteins were stained with stepavidin-horseradish peroxidase conjugate (Amersham (Arlington Heights, Ill.)) and developed using the Renaissance chemiluminescence system.

Determination of Antibody Binding Affinity

The binding affinities of the antibodies to resting, ligand occupied and activated gel filtered platelets were determined using a flow cytometric method developed for measuring the kinetics of binding parameters to GPII/IIIa on platelets. Prior to the Kd determination of mAb10-758 and mAb15-758, the Kd of the FITC labeled goat anti-mouse secondary antibody used in the flow cytometry method had to be determined. Briefly, gel filtered platelets were diluted in flow cytometry buffer (10 mM Hepes, 5 mM KCl, 145 mM NaCl and 1 mM MgCl) to a final concentration of 2×10$^7$ cells/mL, which gives a range of receptor concentration from 2.0–5.0 nM. The platelets were then incubated with saturating concentrations (10 nM) of the anti GP IIb/IIIa monoclonal antibody CD61 (Immunotech (Westbrook, Me.)) for 1 hour at room temperature. Increasing amounts of FITC conjugated goat anti-mouse were added to 200 µl of platelet suspension and incubated for 1 hour at room temperature. Following incubation, the samples were analyzed using FACScaliber flow cytometry system measuring fluorescent intensity of 20000 cells. Kenetic determinations were done using Sigma Plot software from Jendel Scientific. A value of 32 nM was determined for the FITC anti-mouse secondary antibody. Based on this result 150 nM of FITC conjugated goat anti-mouse antibody was used in all subsequent Kd determinations.

The binding affinities of mAb10-758 and mAb15-758 were determined by incubating 200 µL of 2×10$^6$ GFP/mL (gel filtered platelets/mL) with increasing concentrations of antibody for 1 hour at room temperature. For the ligand treated samples the platelets were incubated with 1 µM of 2-(S)-(3-pyridylsulfonyl)amino-3-N-[5-[2-(4-piperidinyl)ethyl]-thienothiophene-2-carboxamide]propionic acid for 15 minutes prior to antibody addition. Incubation of the GFP with 20 µM ADP (Chrono-log Corporation (Havertown, Pa.)) for 5 minutes prior to antibody addition provided the activated platelet sample. 150 nM of FITC conjugated goat anti-mouse secondary antibody was added to the sample and incubated for 1 hour followed by analysis using flow cytometry. The light scatter and fluorescent intensity of 20000 cells was collected using logarithmic gain. Nonspecific secondary antibody binding was corrected for by subtracting the fluorescent mean/platelet value of secondary antibody binding to platelets in the absence of primary antibody.

The binding affinities of FITC-labelled CD61 as well as CD41a (Dako Corporation (Carpinteria, Calif.)) to resting gel filtered platelets were determined in a similar manner.

Flow Cytometry Binding Assays on Platelets

To study the effect of receptor occupation with various fibrinogen receptor antagonist on antibody binding, 100 µL of 2×10$^8$ GFP/mL in platelet buffer, were pretreated for 15 minutes with 1 µM of ligand: previously defined compound A, tirofiban, compound B, compound C, compound D, RO44-9883 and echistatin, or 1 mM RGDS diluted in flow cytometry buffer. 100 nM of purified antibody was added and incubated for 1 hour at room temperature. The platelet bound antibodies were separated from free antibodies by centrifugation in the presence of 100 µM PGE$_1$ followed by resuspension in flow cytometry buffer containing 100 nM of FITC conjugated goat anti-mouse antibody, incubated for 1 hour at room temperature and analyzed using flow cytometry. The light scatter and fluorescence intensity of 20000 cells was collected using logarithmic gain. For analysis of binding to activated platelets the platelets were activated with 20 µM of ADP for 5 minutes at room temperature prior to antibody addition.

To study the influence of complex denaturization on antibody binding the platelets were treated with of 5 mM EGTA pH 8.0 at 37° C. (Shattil et al. (1985) *Blood* 66, 92–98) prior to the addition of 100 nM purified antibody addition and further incubation for 1 hour at 37° C.

PAC-1 (Shattil et al. (1985) *J. Biol. Chem.* 260, 11107–11114) binding studies were done using 20 µg/mL FITC conjugated PAC-1 (University of Pennsylvania Cell Center (Philadelphia, Pa.)) diluted in PBS. 25 µL of resting 1×10$^8$ GFP/mL, in flow cytometry buffer containing 1 mM CaCl, was combined with 100 nM of antibody and FITC conjugated PAC-1 to a final volume of 100 µL. The sample was incubated for 1 hour at room temperature. Following incubation the cells were diluted to 300 µL in flow cytometry buffer immediately before flow cytometry analysis. Contol PAC-1 binding to activated platelets was tested by first activating the receptors with either 1 nM thrombin or 20 µM ADP. Some samples were pretreated with activation inhibitors 100 µM PGE$_1$, 20 µg/ml apyrase (Sigma Chemical Company (St. Louis, Mo.)) and 10 µM PGI$_2$ (BioMol (Plymouth Meeting, Pa.)) prior to antibody addition or platelet activation with ADP or thrombin.

Cell Binding Assays

Binding of the antibodies to various cell lines was analyzed by single-color flow cytometry. Cells were harvested with trypsin/EDTA, washed three times in Dulbecco's phosphate buffer saline and diluted to 2×10$^5$ in flow cytometry buffer containing 1 mM CaCl. For compound treated sample, 1 µM of compound was added 15 minutes prior to the addition of 100 nM of mAb3-758, mAb10-758 or mAb15-758. Samples were incubated for 40 minutes at room temperature. 100 nM of FITC conjugated goat anti-mouse was added directly to the sample and incubated for 1 hour at room temperature followed by flow cytometry analysis.

Clot Retraction

Inhibition of clot retraction by the monoclonal antibodies was done essentially as described by Chen et al. (Chen et al. (1995) *Blood* 86, 2606–2615). Briefly, 100 µL of 2×10$^8$ GFP/mL were incubated with 100 nM of the test monoclonal antibody for 30 minutes followed by the addition of DMEM containing HEPES and calcium and human platelet poor fibronectin-depleted plasma. Clot retraction was initiated by the addition of 1 nM thrombin. Sample were incubated for 2 hours at 37° C. and clot retraction was estimated visually.

Platelet Aggregation

Aggregation by platelets stir red (1000 rpm) at 37° C. was assayed using the Chrono-Log Lumiaggregometer. Antibody mAb3-758, mAb10-758 or mAb15-758 were added to 250 µL of 2×10$^8$ GFP/mL, in platelet buffer containing 2 mM CaCl, in the absence or presence of 20 µM ADP followed by the addition of 200 µg/mL fibrinogen. In some experiments PGE$_1$, apyrase and PGI$_2$ were included as activation inhibitors. Changes in light transmittance were recorded and transferred to Microsoft Excel for data plotting. For the determination of EC$_{50}$ and IC$_{50}$ of mAb3-758 and mAb10-758, respectively, control aggregations Pusing ADP alone were performed with each set of concentrations tested.

Fibrinogen Binding

Fibrinogen (Sigma Chemical Company (St. Louis, Mo.)) was labeled with a fluorescence moiety as described in Xia et al. (1996) *Br. J. Haematol.* 93, 204–214). 100 µL of 1×10$^8$ GFP/mL in flow cytometry buffer containing 2 mM CaCl$_2$ were preincubated with 100 nM of antibody for 30 minutes prior to the simultaneous addition of 40 µM ADP and 50 µg/ml FITC fibrinogen. Following incubation for 15 minutes the platelet suspension was diluted 1:10 in flow cytometry buffer and measured on the flow cytometer.

Antibody Competition

The Kd of all antibodies to resting gel filtered platelets was determined using the flow cytometry method previously described. All antibodies were used at saturating concentrations based on their Kd. 2×10$^7$ GFP/mL were either preincubated with 100 nM of mAb3-758, mAb10-758 or mAb15-758 prior to the addition of 100 nM FITC conjugated CD61 (Dako (Carpinteria, Calif.)); or 50 nM of FITC conjugated CD41a (Dako (Carpinteria, Calif.)); or the antibodies were co-incubated. Following incubation for 1 hour at room temperature the sample were analyzed by flow cytometry. A decrease in the fluorescent intensity was used as a measure of antibody competition.

Characterization of Anti-LIBS Antibodies

Monoclonal antibodies were generated by immunizing BALB/c mice with purified α$_{IIb}$β$_3$ in the presence of the RGD-mimetic 2-(S)-(3-pyridylsulfonyl)amino-3-N-[5-[2-(4-piperidinyl)ethyl]-thienothiophene-2-carboxamide] propionic acid. The resulting 33 hybridomas yielded 18 supernates which contained antibodies reactive against immobilized purified GPIIb/IIIa in an ELISA screen (absorbance 405 nm greater then 0.5). Flow cytometry analysis for antibodies that had preferential binding to ligand occupied receptors revealed that seven of the hybridomas showed at least a 20% increase in binding in the presence of 20 µM 2-(S)-(3-pyridylsulfonyl)amino-3-N-[5-[2-(4-piperidinyl)ethyl]-thienothiophene-2-carboxamide] propionic acid. Five of these were chosen for single cell cloning (Table 2).

TABLE 2

Single cell clones

| Parental Hybrid | % Increase in Binding | Single CellClone | Relative Fluorescence |
|---|---|---|---|
| BH5 | 21 | mAb1-758 | 1.01 |
|  |  | mAb2-758 | 1.05 |
|  |  | mAb3-758 | 1.45 |
|  |  | mAb4-758 | 0.87 |
| BH6 | 36 | mAb5-758 | 1.27 |
|  |  | mAb6-758 | 0.9 |
|  |  | mAb7-758 | 1 |
|  |  | mAb8-758 | 1.3 |
| DD6 | 52 | mAb9-758 | 1.02 |
|  |  | mAb10-758 | 2.11 |
|  |  | mAb11-758 | 1.94 |
|  |  | mAb12-758 | 2.02 |
| FB3 | 272 | mAb13-758 | 3.35 |
|  |  | mAb14-758 | 3.65 |
|  |  | mAb15-758 | 3.5 |
|  |  | mAb16-758 | 4.15 |
| EF11 |  | mAb33-758 | 1.96 |
|  |  | mAb34-758 | 2.31 |
|  |  | mAb35-758 | 2.33 |
|  |  | mAb36-758 | 2.32 |

In Table 2, percent increase in binding was calculated following flow cytometry analysis on $2 \times 10^8$ GFP/mL in the presence or absence of 20 mM 2-(S)-(3-pyridylsulfonyl)amino-3-N-[5-[2-(4-piperidinyl)ethyl]-thienothiophene-2-carboxamide]propionic acid and 5 uL of hybridoma supernate. Values were calculated as $$\frac{\text{treatment} - \text{control}}{\text{control}} \times 100\%$$

Relative fluorescence was determined following cytometry analysis on $2 \times 10^8$ GFP/ml in the presence or absence of 20 mM 2-(S)-(3-pyridylsulfonyl)amino-3-N-[5-[2-(4-piperidinyl)ethyl]-thienothiophene-2-carboxamide] propionic acid and 5 uL of supernate. Values were calculated as $$\frac{\text{treatment fluorescence}}{\text{control fluorescence}}$$

Single cell cloning yielding 20 antibodies, 9 of which showed at least a two fold increase in binding to ligand occupied receptors and could be potential anti-LIBS antibodies (Table 2). Two of these antibodies designated mAb10-758 and mAb15-758, and one antibody with less then a two fold increase, mAb3-758, were chosen for further examination (Table 3).

TABLE 3

Antibody characteristics

| mAb | Relative Fluorescence increase on resting GFP | Isotype | Subunit | $K_D$ presence of ligand resting GFP | $K_D$ on activated platelets | $K_D$ absence of ligand resting GFP |
|---|---|---|---|---|---|---|
| 3-758 | 1.45 | $G_1K$ | * | 0.47 | 0.30 | 0.39 |
| 10-758 | 2.11 | $G_1K$ | $\beta_3$ | 7.3 | 23.5 | 10.8 |
| 15-758 | 3.5 | $G_1K$ | $\beta_3$ | 17.8 | >500 | >500 |

* no reaction on western blot

Relative fluorescence increase in binding to $2 \times 10^8$ GFP/mL is calculated as described above. Subunit specificity was determined by western analysis as described above. $K_D$ values were determined as described above.

Subunit and Binding Specificity

The binding specificity of the antibodies was examined by Western blotting against purified GPIIb/IIIa and immunoprecipiation of surface biotinylated receptors.

mAb10-758 and mAb15-758 recognized a band that migrated to the position of $\beta_3$ subunit under nonreducing conditions. In contrast, mAb3-758 showed no band recognition in Western blots. These results suggest that mAb3-758 may require an integrin complex or that the epitope for the antibody is not present under these conditions.

To further examine the heterodimer requirements as well as integrin specificity of the antibodies, immunoprecipitation of biotinylated surface proteins from the cell lysates of gel filtered platelets, HEL cells (Tabilio et al. (1984) *The EMBO J.* 3, 453–459), HUVEC cells (Ginsberg et al. (1987) *J. Biol. Chem.* 262, 5437–5440), HEK-293 cells; and two recombinant cell lines HEK-$\alpha_v\beta_3$ and HEK-$\alpha_{IIb}\beta_3$ cells was performed. Table 4 lists the major integrins contained in each cell line.

TABLE 4

Major integrins in cell lines used in immunoprecipitation

| Platelets | HEL | HUVEC | 293 | HEK-293 | IIbβ3 |
|---|---|---|---|---|---|
| $\alpha_{IIb}\beta_3$ | $\alpha_{IIb}\beta_3$ | $\alpha_v\beta_3$ | $\alpha_v\beta_1$ $\alpha_5\beta_1$ $\alpha_4\beta_1$ $\alpha_2\beta_1$ | $\alpha_v\beta_3$ | $\alpha_{IIb}\beta_3$ |

Integrins on platelets, HEL, HUVEC and 293 cell lines are endogenous. Integrins on HEK-293 and IIbβ3 cell lines are recombinant.

All three antibodies immunoprecipitated two proteins from HEL cells with mobilities identical to surface labeled proteins from platelets and immunoprecipitated two proteins from HUVEC cells with mobilities corresponding to the $\alpha_v$ and $\beta_3$ proteins. None of the antibodies immunoprecipitated proteins from the HEK-293 cells. Taken together these results indicated that these antibodies recognize the $\beta_3$ subunit of $\alpha_{IIb}\beta_3$ and/or $\alpha_v\beta_3$ when the two subunits are in an endogenous cell system. However, in the recombinant cell lines HEK-II$_b\beta_3$ and HEK-$\alpha_v\beta_3$ only mAb10-758 was able to immunoprecipitate recombinant $\alpha_{IIb}$ and $\beta_3$ proteins from HEK-II$_b\beta_3$ cells and the $\alpha_v$ or $\beta_3$ proteins from HEK-$\alpha_v\beta_3$ cells and indicate that the antibody does not require the $\alpha_{IIb}\beta_3$ heterodimer for antibody binding. mAb3-758 did not immunoprecipitate any proteins from the HEK-$\alpha_v\beta_3$, and mAb15-758 was only able to immunoprecipitate the $\beta_3$ subunit from HEK-$\alpha_v\beta_3$. Unpublished results indicate that the receptors in the recombinant HEK-II$_b\beta_3$ and HEK-$\alpha_v\beta_3$ cells are conformationally distinct from their endogenous counterparts in platelets or HEL cells and HUVEC cells respectively. These conformational differences could indicate that mAb3-758 and mAb15-759 recognize the $\beta_3$ subunit, and that the subunit has to be in a specific conformation in order for the antibody to bind.

Binding of the Antibodies to Resting Platelets and the Influence of Receptor Occupancy The binding affinity of the monoclonal antibodies to resting and unoccupied receptors, resting ligand occupied receptors and ADP activated platelets was determined using a flow cytometry method previously described. Examination of the Kd values (Table 3) and histograms of cell count versus fluorescence reveal that monoclonal antibody mAb3-758 has a high binding affinity to resting platelets that is not influenced by the presence of ligand, whereas mAb10-758 has a high binding affinity to resting platelets which is slightly increased on ligand occupied receptors, and mAb15-758 binding to resting platelets is very weak, and is greatly increased in the presence of 1 μM 2-(S)-(3-pyridylsulfonyl)amino-3-N-[5-[2-(4-piperidinyl)ethyl]-thienothiophene-2-carboxamide]propionic acid.

The binding characteristics of mAb3-758 and mAb10-758 to resting platelets and ligand occupied platelets indicate that the epitope for these antibodies is fully exposed on resting platelets. However, the binding characteristics of mAb15-758 to resting unoccupied and occupied receptors raises the possibility that the epitope for mAb15-758 is cryptic in resting platelets and is exposed by ligand induced conformational changes.

To test the hypothesis the GPIIb/IIIa complex was irreversibly denatured by the addition of 5mM EGTA at 37° C. Irreversible disassociation of the GPIIb/IIIa complex with 5 mM EGTA abolished mAb3-758 binding to resting platelet. These results support the immunoprecipitation data that indicate that the epitope for mAb3-758 is exposed on the $\beta_3$ subunit but requires a particular conformation of the subunit. Disassociation of the GPIIb/IIIa complex with EGTA did not abolish mAb10-758 binding again confirming that the epitope for this antibody is exposed on resting platelets. In contrast, mAb15-758 binding was enhanced under these conditions. These data support the previous findings that indicate that the epitope for mAb15-758 is not exposed on resting unoccupied receptors, but is exposed due to a conformational change in the receptor. Complete disassociation of the complex under EDTA treatment was confirmed by diminished binding of the complex dependent antibody CD41a to background levels.

Platelet activation by agonists also cause conformational changes of the surface exposed domains of the GPII/IIIa receptor (Kieffer et al. (1991) *J. Cell. Bio.* 113, 451–461). Binding of all three antibodies was not enhanced by activation of resting platelets by 20 μM ADP. Therefore, the conformational changes in the GPIIb/IIIa complex due platelet activation are different then the conformational changes caused by ligand binding and are not sufficient to enhance antibody binding. Similar results were shown for other anti-LIBS antibodies (Kouns et al. (1990) *J. Biol. Chem.* 265, 20594–20604).

Effects of Receptor Occupancy by Various Fibrinogen Receptor Antagonists on Antibody Binding One characteristic of anti-LIBS antibodies is increased affinity for ligand occupied GPIIb/IIIa. In order to determine if various ligands that can bind to GPIIb/IIIa induce a universal conformational change which can be recognized by an anti-LIBS antibody, a series of GPIIb/IIIa antagonist, ranging in structure and affinities (Table 1), were tested for their influence on mAb3-758, mAb10-758 and mAb15-758 binding. Flow cytometric binding measurements showed that all potent GPIIb/IIIa ligands were able to induce the expose of mAb10-758 and mAb15-758. None of the ligands enhanced mAb3-758 binding. These finding reveal that the neo-epitope is induced by multiple ligands including RO-44-9883, a compound which had previously been reported to not induce a LIBS binding site for mAbD3 (Steiner et al. (1993) *Thrombosis and Haemostasis* 782). These results show that potentially any ligand upon bind to GPIIb/IIIa has the ability to induce conformational changes in the receptor. Similar results were seen in binding studies on platelet rich plasma.

Binding of the Antibodies to Integrins in Cell Lines

The GPIIb/IIIa complex expressed on HEL cell is functionally distinct from the receptor expressed in platelets in terms of ligand binding (Kieffer et al. (1991) *J. Cell. Bio.* 113, 451–461). These functional differences are partially due to differences in the conformation of $\alpha_{IIb}\beta_3$ is HEL cells versus platelets (Jennings et al. (1996) *Blood Cells Molecules and Diseases* 22, 23–35). To determine if the antibody binding properties are influence by receptor conformation cell binding studies were performed. Histograms of antibody binding to HEL cells indicate that all three antibodies bind to HEL cells, but that the addition of ligand no longer increased the affinity of mAb15-758 for the receptors. Therefore, even though the antibodies are able to recognize the GPIIb/IIIa receptor in various microenvironments ligand binding does not alter the conformation of $\alpha_{IIb}\beta_3$ in HEL cells in the same was as ligand binding in platelets. Thus supporting the previous findings that the GPIIb/IIIa receptor expressed in HEL cells is functionally and conformationally distinct from the GPIIb/IIIa receptor in platelets.

RGD-containing ligands are also recognized by other integrins including the vitronectin receptor (Pytela et al. (1986) *Science* 263, 12397–12402). To determine if the occupancy of the vitronectin receptor by ligand also induced LIBS expression, the binding of the antibodies to $\alpha_v\beta_3$ expressed in recombinant HEK-$\alpha_v\beta_3$ cells and Huvec cells was examined. Both cell lines have minimal expression of $\alpha_{IIb}\beta_3$. Histogram analysis of cell number versus fluorescence intensity showed the addition of ligand (1 μM echistatin) increased the binding of the potential anti-LIBS antibodies mAb15-758 and mAb10-758 to $\alpha_v\beta_3$ in HEK-$\alpha_v\beta_3$, but not the control antibody, mAb3-758. However, this was not observed when for the endogenous receptors in Huvec cells. Only mAb10-758 bound to $\alpha_v\beta_3$ in this cells. The binding differences between the endogenous and recombinant cell lines again supports the idea that the receptors in these two cell lines are conformationally distinct.

Influence of Antibodies on Platelet Aggregation and Clot Retraction

Several anti-LIBS antibodies have been shown to influence platelet aggregation and clot retraction (Kouns et al. (1990) *J. Biol. Chem.* 265, 20594–20604; Frelinger et al. (1991) *J. Biol. Chem.* 266, 17106–17111; and Frelinger et al. (1990) *J. Biol. Chem.* 265, 6346–6352). The ability of mAb3-758, mAb10-758 and mAb15-758 to influence aggregation of gel filtered platelets was assayed by luminaggregometry. 50 nM mAb3-758 added to stirring gel filtered platelets preincubated with 200 μg/mL fibrinogen inhibited ADP stimulated platelet aggregation with an IC$_{50}$ 10.2 nM. Platelets treated with mAb3-758 prior to ADP addition had a 1.3% aggregation response, in contrast to control platelet that had a 69.6% aggregation response to the addition of 20 μM ADP alone.

Like other anti-LIBS antibodies (Kouns et al. (1990) *J. Biol. Chem.* 265, 20594–20604; Frelinger et al. (1991) *J. Bio. Chem.* 266, 17106–17111), 100 nM mAb10-758 was able to stimulate an agonist independent platelet aggregation response of 27.1% with an EC$_{50}$ 35 nM compared to ADP stimulated platelet aggregation response of 69.6% with an EC$_{50}$ 1.7 μM. 1 μM mAb15-758 also stimulated an ADP independent platelet aggregation response of 25%. No EC$_{50}$ value was determined for mAb15-758. Platelet aggregation stimulated by mAb10-758 and mAb15-758, like ADP induced aggregation, is dependent on the presence of fibrinogen as evident by blockage of aggregation by a potent fibrinogen receptor antagonist. Following incubation with 10 μM of antagonist, mAb10-758 induced a 2.2% aggregation response, mAb15-758 a 4.8% aggregation response and ADP a 2.5% aggregation response as compared to 26.9%, 31% and 69.6% respectively in control platelets. However, mAb10-758 and mAb15-758 stimulated platelet aggregation is not dependent upon platelet activation. Platelets that were pretreated with a mixture of $PGE_1$, $PGI_2$, and apyrase prior to the addition of 100 nM mAb10-758 or 1 μM mAb15-758 had a 19.3% and 19% response respectively, as compared to the 27.1 % and 25% aggregation response in control platelets upon antibody addition. Inhibitor treated platelets had a 3.3 % aggregation response following ADP addition, in contrast to 69.6% for control platelets.

Since mAb3-758 blocks platelet aggregation it was of interest to test if this antibody also blocks clot retraction. Clot retraction was blocked mAb 13-758. Whereas the antibodies which do not inhibit platelet aggregation namely, mAb10-758 and mAb15-758, also do not inhibit clot retraction.

Platelet function is mediated by fibrinogen binding to activated platelets (George, et al. (1984) *N. Eng. J. Med.* 311, 1084). Therefore it was ascertained if mAb3-758 was inhibiting the processes of platelet aggregation and clot retraction by blocking fibrinogen binding to activated platelets. Previous work has shown that fibrinogen binding can be examined using FITC labeled fibrinogen and flow cytometry (Heilmann et al. (1994) *Cytometry* 17, 287–293). GFP that were preincubated with 100 nM of mAb3-758 prior to activation with ADP and the addition of FITC-Fg. Decreases FITC fibrinogen binding was observed in the samples that were pretreated with mAb3-758 indicating that the antibody does block fibrinogen binding to activated platelets.

Influence of Antibodies on PAC1 Binding

PAC-1 is a murine monoclonal antibody that mimics RGD containing ligands and shows preferential binding to agonist stimulated platelets (George, et al. (1984) *N. Eng. J. Med.* 311, 1084; Heilmann et al. (1994) *Cytometry* 17, 287–293). This antibody was used to characterized the activation state of the GPIIb/IIIa complex post antibody binding. Results show that PAC-1 does not bind to unactivated platelets, however activation of the platelets with agonist or incubation with 100 nM mAb10-758 or 1 μM mAb15-758 induced FITC conjugated PAC1 binding to GFP. mAb3-758 did not induce PAC-1 to bind to resting platelets. These results would suggest that mAb10-758 and mAb15-758 either alter the conformation of GPIIb/IIIa and allow PAC-1 to bind to resting platelets or that the antibodies activate the receptor. To determine if platelet activation or a conformational change is involved in the ability of mAb10-758 and mAb15-758 to induce PAC-1 binding to resting platelets the platelets were pretreated with a combination of activation inhibitors, namely $PGE_1$, $PGI_2$ and apyrase prior to the addition of antibody or agonist. The inhibitors completely blocked the ability of ADP to promote PAC-1 binding, however PAC-1 binding to antibody treated platelets was only partially blocked by the addition of inhibitors. These results support that the antibodies induce a conformational change in the receptor which allows PAC-1 to bind.

Competition Between Other GPIIb/IIIa Antibodies:

To elucidate the location of the epitope for the antibodies, competition analysis between the monoclonal antibodies and several other known GPIIb/IIIa antibodies was performed. Table 5 shows the results of the competition studies.

TABLE 5

Competition analysis between monoclonal antibodies and other GP IIb/IIIa antibodies

| mAb | CD61 ($\beta_3$) | CD41a (IIb complex) | PAC-1 |
|---|---|---|---|
| 3-758 | No | No | Yes |
| 10-758 | No | No | No |
| 15-758 | No | No | No |

"Yes" means the antibody competes with the monoclonal antibody. "No" means the antibody does not compete with the monoclonal antibody.

Competition analysis between monoclonal antibodies and other anti-GPIIb/IIIa antibodies was performed on $2\times10^7$ GFP/ml using flow cytometry.

PAC-1 blocks fibrinogen mediated platelet aggregation. Therefore, it was of interest to test if mAb3-758 could compete with PAC-1 binding to platelets. Pre-incubation of activated platelets with 100 nM of mAb-3 reduced PAC-1 binding but did not completely block binding.

The epitopes for CD61 and CD41a are located on the $\beta_3$ and $\alpha_{IIb}$ subunit of GPIIb/IIIa respectively. Competition studies between these two antibodies and all three monoclonal antibodies revealed that none of the antibodies competed with CD61 or CD41a, indicating that these antibodies recognize an epitope that does not overlap the epitope for CD61 or CD41a.

Preparation of Humanized Monoclonal Antibodies

General procedures for making of hybridoma cell lines for the purpose of producing monoclonal antibodies are well known. Procedures for humanizing monoclonal antibodies are exemplified in U.S. Pat. No. 5,565,354, which describes procedures for obtaining human monoclonal antibodies effective in particular against hepatitis B surface antigen (HBsAg), such antibodies being prepared according to a generally applicable method described by the applicant in *Hybridoma* (1983) v. 2 n. 4, p. 361 and British Patent Publication 2,113,715A. It has been shown, for example, that a hybridoma cell line comprising a parent rodent immortalizing cell, such as a murine myeloma cell, e.g., SP-2, fused to a human partner cell, results in an immortalizing xenogeneic hybridoma cell. This xenogeneic hybridoma cell may be fused to a cell capable of producing an anti-HBsAg human antibody, resulting in a novel trioma cell line capable of generating human antibody effective against such antigen in the human. Alternately, when greater stability is desired, a trioma cell line which preferably no longer has the capability of producing its own antibody is made and this trioma is then fused with a further cell capable of producing useful against said antigen so as to obtain a still more stable hybridoma (quadroma) which produces antibody against the antigen.

In U.S. Pat. No. 5,565,354, a xenogeneic hybridoma referred to as SPAZ 4 was prepared from drug resistant cell line SP-2 obtainable, e.g., from the NIGMS Human Genetic Mutant Cell Responsitory Ref. GM35669A (see United States DHHS 1982 Catalog of Cell Lines). Preparation of SPAZ 4 is summarized as follows. The SP-2 cell line is fused with normal human peripheral lymphocytes by conventional techniques. A large number of hybrids is obtained and, after approximately five weeks, five clones are selected which show fast growth and no antibody production. These cells are selected for resistance to 8-azaguanine and with three of these lines it is possible to obtain mutants which are resistant to 20 μg/ml of 8-azaguanine. These cells are at the same time sensitive to Hypoxanthine-Aminopterin-Thymidine (HAT)

medium which showed that they had lost their ability to produce hypoxanthine phosphoribosyl transferase. One of these cell lines is SPAZ 4.

Cell line SPAZ 4 may be fused with cells obtained from the blood of persons immunized with hepatitis B vaccine to obtain hybridoma cell lines which provide positive cultures when standard selection procedures are used involving binding of antibodies to relevant viral antigens. Positive cultures may be placed through a second selection process in which different subtypes of the virus are used for antigen preparation. This provides us an opportunity to pinpoint the exact antigenic determinant recognized by the antibody.

The cell lines resulting from the fusion of a xenogeneic hybridoma and the human monoclonal antibody producing cell (trioma) are therefore useful in providing monoclonal antibodies capable of effective activity in neutralizing a virus causing hepatitis, and the antibodies can therefore prevent the spread of hepatitis through, e.g., blood transfusion. They can also be used to give initial protection to newborn babies or exposed individuals earlier than a vaccine could be effective. Anti-hepatitis antibodies may be used to protect immunosuppressed patients, including transplantation patients, from recurrent hepatitis. This is most significant in cases of hepatitis B positive liver recipients. Further, the antibodies can be used in diagnostic assays. The antibodies can be humanized using humanizing techniques generally known in the art.

The cell line DD6, which produces mAb10-758, has been placed on deposit at the American Type Culture Collection, 12301 Parklawn Drive, Rockville, Md., 20852 on Aug. 27, 1997 under the ATCC designation HB-12393. The cell line FB3, which produces mAb15-758, has been placed on deposit at the American Type Culture Collection, 12301 Parklawn Drive, Rockville, Md., 20852 on Aug. 27, 1997 under the ATCC designation HB-12394. These deposits were made under the provisions of the Budapest Treaty of the International Recognition of the Deposit of Microorganisms for the Purposes of Patent Procedure and the Regulations thereunder (Budapest Treaty). Maintenance of a viable culture is assured for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention rights granted under the authority of any government in accordance with its patent laws.

EXAMPLE 1

GP IIb/IIIa Antagonist Treatment and Method for Identifying a Patient at Risk to Developing GP IIb/IIIa Antagonist-induced Thrombocytopenia A patient with acute coronary ischemic syndromes receives coronary revascularization with angioplasty. Aspirin is administered in a dose of 325 mg at least two hours before angioplasty, and daily thereafter. Heparin is given intravenously in an initial bolus dose of 10,000 to 12,000 units followed by incremental bolus doses of up to 3000 units at 15-minute intervals, but no more than 20,000 units is given during the procedure. The goal is to keep the activated clotting time between 300 and 350 seconds during the operation. Heparin is continued by constant infusion for at least 12 hours to maintain the activated partial-thromboplastin time at 1.5 to 2.5 times the control value. Aspirin is required at discharge in a dose of 325 mg per day.

The patient is scheduled to receive an oral tablet containing 15 mg of the fibrinogen receptor GP IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid, described in WO 94/18981. Prior to initiation of treatment with the antagonist, the patient is screened to determine whether the patient is at risk to developing thrombocytopenia induced by the antagonist.

A plasma sample is drawn from the patient and incubated with a GPIIb/IIIa receptor:receptor antagonist complex and a detectable monoclonal antibody which recognizes induced binding sites formed on the GP IIb/IIIa receptor following association of the fibrinogen receptor antagonist with the GP IIb/IIIa receptor. Analysis of the reaction product resulting from incubation indicates that the detectable monoclonal antibody cannot be detected on the complex. Failure of the monoclonal antibody to bind to the complex in the presence of the patient's plasma indicates that the patient's plasma contains an antibody which recognizes the binding sites formed following association of the fibrinogen receptor antagonist with the receptor. The presence of this antibody in the patient's plasma identifies the patient as at risk to developing thrombocytopenia following treatment with the antagonist.

EXAMPLE 2

GP IIb/IIIa Antagonist Treatment and Method for Identifying a Patient not at Risk to Developing GP IIb/IIIa Antagonist-induced Thrombocytopenia A patient with acute coronary ischemic syndromes receives coronary revascularization with angioplasty. Aspirin is administered in a dose of 325 mg at least two hours before angioplasty, and daily thereafter. Heparin is given intravenously in an initial bolus dose of 10,000 to 12,000 units followed by incremental bolus doses of up to 3000 units at 15-minute intervals, but no more than 20,000 units is given during the procedure. The goal is to keep the activated clotting time between 300 and 350 seconds during the operation. Heparin is continued by constant infusion for at least 12 hours to maintain the activated partial-thromboplastin time at 1.5 to 2.5 times the control value. Aspirin is required at discharge in a dose of 325 mg per day.

The patient is scheduled to receive an oral tablet containing 15 mg of the fibrinogen receptor GP IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid, described in WO 94/18981. Prior to initiation of treatment with receptor antagonist, the patient is screened to determine whether the patient is at risk to developing thrombocytopenia induced by receptor antagonist.

A plasma sample is drawn from the patient and incubated with a GPIIb/IIIa receptor:receptor antagonist complex and a detectable monoclonal antibody which recognizes induced binding sites formed on the GP IIb/IIIa receptor following association of the fibrinogen receptor antagonist with the GP IIb/IIIa receptor. Analysis of the reaction product resulting from incubation indicates that the detectable monoclonal antibody is detected on the complex. Binding of the detectable monoclonal antibody to the complex in the presence of the patient's plasma indicates that the patient's plasma does not contain an antibody which recognizes binding sites formed following association of the fibrinogen receptor antagonist with the receptor. The absence of this antibody in the patient's plasma identifies the patient as not at risk to developing thrombocytopenia following treatment with the antagonist.

It will be understood that the specification and examples illustrate but do not limit the present invention other embodiments within the spirit and scope of the invention will suggest themselves to those skilled in the art.

What is claimed is:

1. A hybridoma cell line selected from the group consisting of DD6, which is designated ATTC HB-12393, and FB3, which is designated ATTC HB-12394.

2. A detectable monoclonal antibody, selected from the group consisting of a monoclonal antibody produced by the hybridoma cell line ATCC HB-12393 and a monoclonal antibody produced by the hybridoma cell line ATCC HB-12394, which specifically recognizes induced binding sites formed on the GP IIb/IIIa receptor following association of a fibrinogen receptor antagonist with the GP IIb/IIIa receptor.

3. A monoclonal antibody of claim 2 produced by the hybridoma cell line ATCC HB-12393.

4. A monoclonal antibody of claim 3 which is mAb10-758.

5. A monoclonal antibody of claim 2 produced by the hybridoma cell line ATCC HB-12394.

6. A monoclonal antibody of claim 5 which is mAb15-758.

* * * * *